US007688437B2

(12) United States Patent
Houck et al.

(10) Patent No.: US 7,688,437 B2
(45) Date of Patent: Mar. 30, 2010

(54) MACHINE FOR INSPECTING GLASS CONTAINERS

(75) Inventors: R. Dean Houck, Addison, NY (US); Richard A. Sones, Cleveland Heights, OH (US); Richard D. Diehr, Horseheads, NY (US); Amir R. Novini, Akron, OH (US)

(73) Assignees: Emhart Glass S.A., Cham (CH); Applied Vision Corporation, LLC, Cuyahoga Falls, OH (US)

( * ) Notice: Subject to any disclaimer, the term of this patent is extended or adjusted under 35 U.S.C. 154(b) by 547 days.

(21) Appl. No.: 11/799,655

(22) Filed: May 2, 2007

(65) Prior Publication Data
US 2008/0273197 A1    Nov. 6, 2008

(51) Int. Cl.
*G01N 21/00* (2006.01)
(52) U.S. Cl. .................. 356/239.4; 382/142; 250/223 B
(58) Field of Classification Search .............. 356/239.4; 382/142
See application file for complete search history.

(56) References Cited

U.S. PATENT DOCUMENTS

| 4,701,612 | A | * | 10/1987 | Sturgill | 356/239.4 |
|---|---|---|---|---|---|
| 4,725,856 | A | * | 2/1988 | Fujikura | 356/239.4 |
| 4,945,228 | A | * | 7/1990 | Juvinall et al. | 356/239.4 |
| 4,958,223 | A | * | 9/1990 | Juvinall et al. | 348/127 |
| 5,020,908 | A | * | 6/1991 | Hermann | 356/239.4 |
| 5,200,801 | A | * | 4/1993 | Juvinall et al. | 356/239.4 |
| 5,661,819 | A | * | 8/1997 | Toyama | 382/142 |
| 5,895,911 | A | * | 4/1999 | Giometti et al. | 356/239.4 |
| 6,104,482 | A | * | 8/2000 | Brower et al. | 356/239.4 |
| 6,211,952 | B1 | * | 4/2001 | Weiland et al. | 356/239.4 |
| 6,275,287 | B1 | * | 8/2001 | Watanabe | 356/239.4 |
| 6,304,323 | B1 | * | 10/2001 | Ishikura et al. | 356/239.4 |
| 7,342,654 | B2 | * | 3/2008 | Laue et al. | 356/239.4 |

* cited by examiner

*Primary Examiner*—Gregory J Toatley, Jr.
*Assistant Examiner*—Juan D Valentin
(74) *Attorney, Agent, or Firm*—Reinhart Boerner Van Deuren s.c.

(57) ABSTRACT

A machine for distinguishing blisters from checks on the finish of a glass container. The center of each captured object in an array is determined by a controller which determines the object centers in a plurality of adjacent bands. The band having the most object centers is determined and the objects in the band having the most object centers are deleted from the rest of the bands. The control repeatedly determines the band of the rest of the bands having the most object centers and deletes the objects in the band of the rest of the bands having the most object centers from the remainder of the bands until the objects in each band are unique. The maximum separation of objects in each band is defined and checks will be differentiated from blisters based on this separation.

15 Claims, 7 Drawing Sheets

MACHINE FOR INSPECTING GLASS CONTAINERS

The present invention relates to machines, which inspect glass containers for defects, and more particularly, to a system which inspects for checks (cracks) in translucent glass containers.

BACKGROUND OF THE INVENTION

In the glass container industry, small cracks, or fracture in the glass are referred to as "check defects". Checks can range from sub millimeters to several hundred millimeters and can be oriented at any direction from vertical to horizontal. Glass is not a crystalline structure by nature, but most cracks propagate roughly along a plane of some orientation in space mostly determined by the shape of the glass at that location. Most of these crack defects will drastically weaken the bottle, often causing it to rupture or to leak. Therefore, it is very likely that a bottle manufacturer will remove a container with a check before it reaches filling plants. Checks appearing near the mouth of the containers are called finish checks. In the glass bottle industry, the term "container finish" refers to the portion of the bottle that defines the mouth, threads or beads, and the ring. The upper surface of the mouth is referred to as the sealing surface.

Another anomaly, which can also be present are bubbles. A bubble results when gas is trapped in the glass. When the bubbles are large they are referred to as a blister and when the bubbles are small, they are referred to as a seed. The presence of bubbles, while affecting the appearance of the bottle, do not necessarily require the rejection of the bottle and an operator may allow such a bottle to be packed. For purposes of this application, the word blister will include a seed.

The following U.S. Pat. Nos. 4,701,612, 4,945,228, 4,958,223, 5,020,908, 5,200,801, 5,895,911, 6,104,482, 6,211,952, and 6,275,287 all relate to devices that detect defects in the finish of a container.

OBJECT OF THE INVENTION

It is an object of the present invention to provide an apparatus for inspecting glass containers, which can differentiate vertical, horizontal, and any other angle cracks (checks) from blisters.

Other objects and advantages of the present portion of this invention will become apparent from the following accompanying drawings, which illustrate, in accordance with the mandate of the patent statutes, a presently preferred embodiment incorporating the principles of the invention

BRIEF DESCRIPTION OF THE DRAWINGS

The invention will become apparent from the following accompanying drawings which illustrate, in accordance with the mandate of the patent statutes, a presently preferred embodiment.

DETAILED DESCRIPTION OF THE PREFERRED EMBODIMENT

Figure 1:
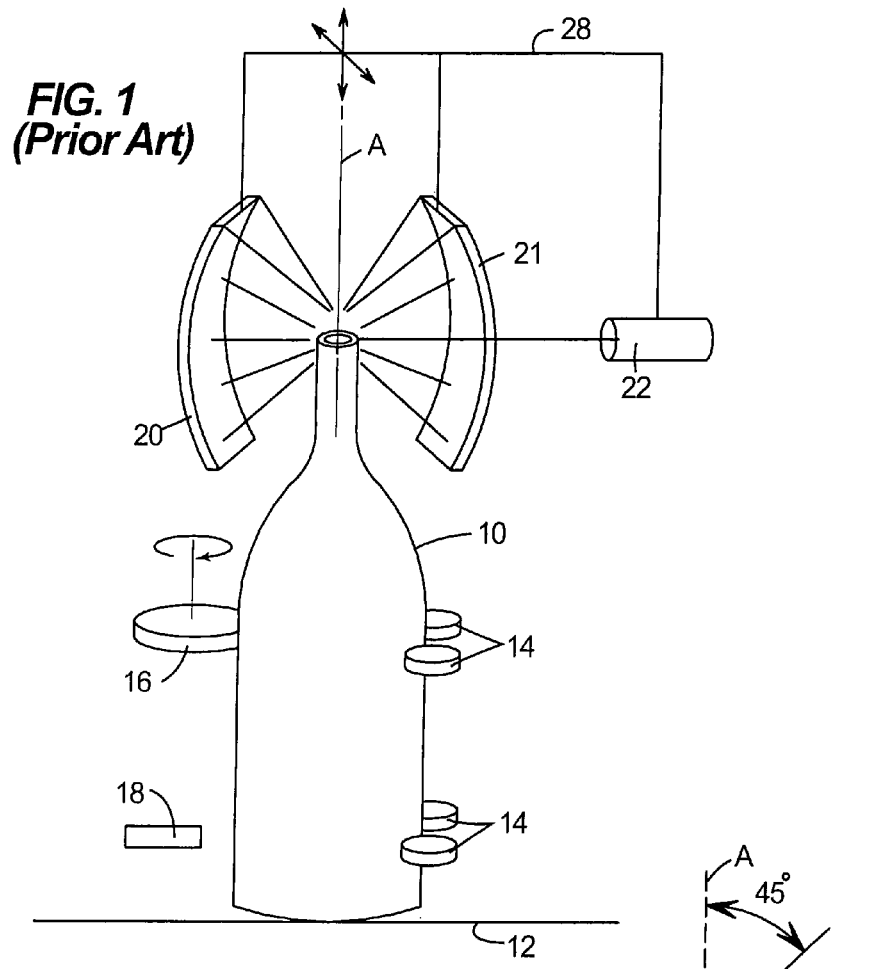
FIG. 1 is an oblique elevational schematic view of a prior art inspection station of a machine for inspecting glass containers for checks and other defects.
Figure 2:
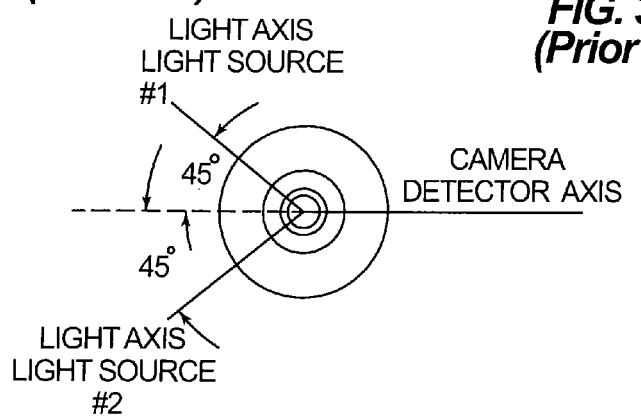
FIG. 2 is a schematic top view of the container at the prior art inspection station showing the light axes of a pair of light sources and the camera.
Figure 3:
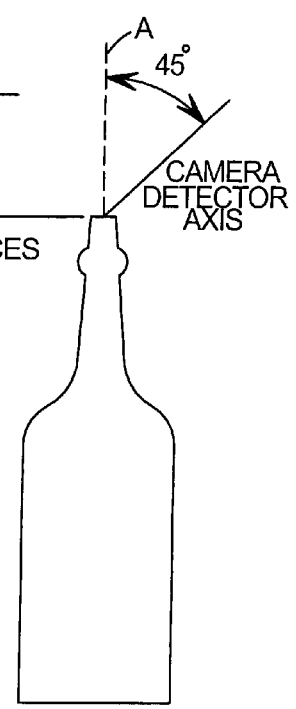
FIG. 3 is a schematic elevational view showing the light axes of the prior art light sources and camera shown in FIG. 2.

In a machine for inspecting glass containers (bottles), the containers 10 are transported vertically along a conveyor 12 to an inspection station illustrated in FIG. 1. The conveyor may be a linear belt or a turret type feed system. A container 10 is engaged by upper and lower rear pairs of idler rollers 14 and a front drive wheel 16 so that rotation of the drive wheel in the clockwise direction will rotate the container in the counterclockwise direction. There is conveyor dwell of sufficient duration at the inspection station so that the container can be rotated more than 360 degrees while inspection takes place. A container present sensor 18 will sense the presence of a container at the inspection station. Conical light sources (Light Source #1/20 and Light Source #2/21) which can be configured from L.E.D.'s, illuminate the finish portion of the container and a Camera/22 images the finish portion. As can be seen from FIGS. 2 and 3, the Light Axis for each light source, which is in the positive "Z" plane of the container, is horizontal, and intersects the axis "A" of the container. The two light axes are orthogonal to each other (the light axes are horizontal and 90 degrees related), and 45 degrees to a vertical plane including the Camera Detector Axis. The Detector Axis for the Camera/22, which is located in the negative "Z" plane, is approximately 45 degrees from horizontal (the camera bisects the horizontal light axes). With this relationship, the camera is looking at a dark field and is ideally seeing only light coming from checks and blisters. The light sources and camera are supported by structure 28 that can be vertically displaced and horizontally displaced to reposition the system for different height/diameter containers.

Figure 4:
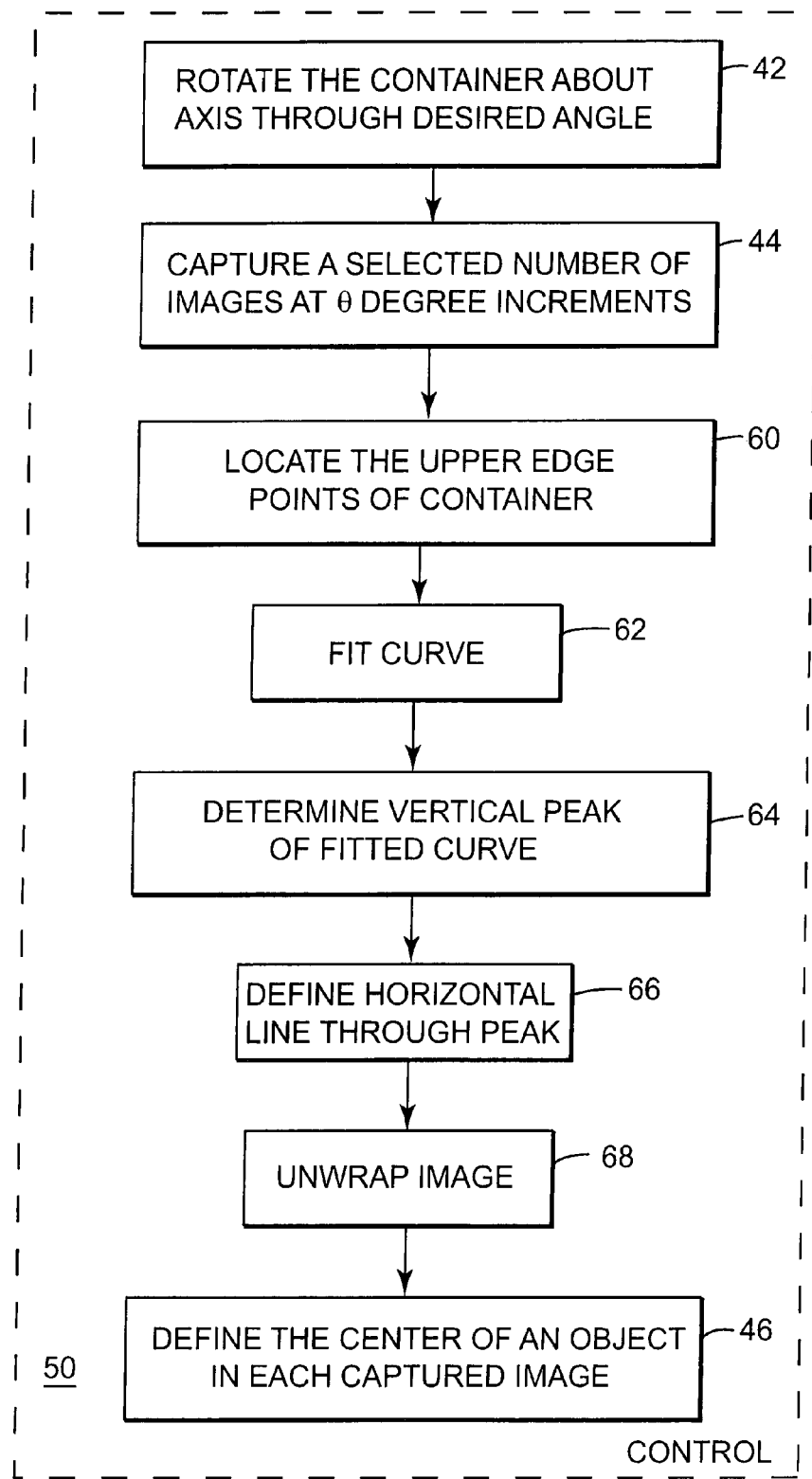
FIG. 4 is a control drawing showing how an unwrapped image is defined.
Figure 5:
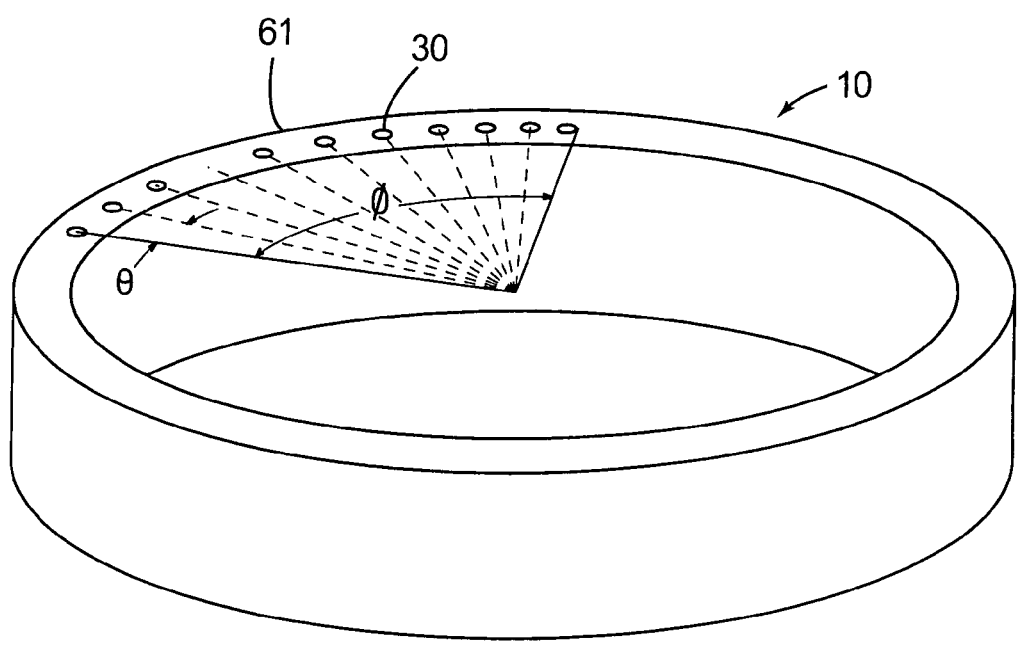
FIG. 5 is a view, taken from the camera, of the finish area of the bottle shown in FIG. 1, illustrating images captured each θ (theta) degrees of rotation of the bottle about its vertical axis through an angle φ (phi)
Figure 6:
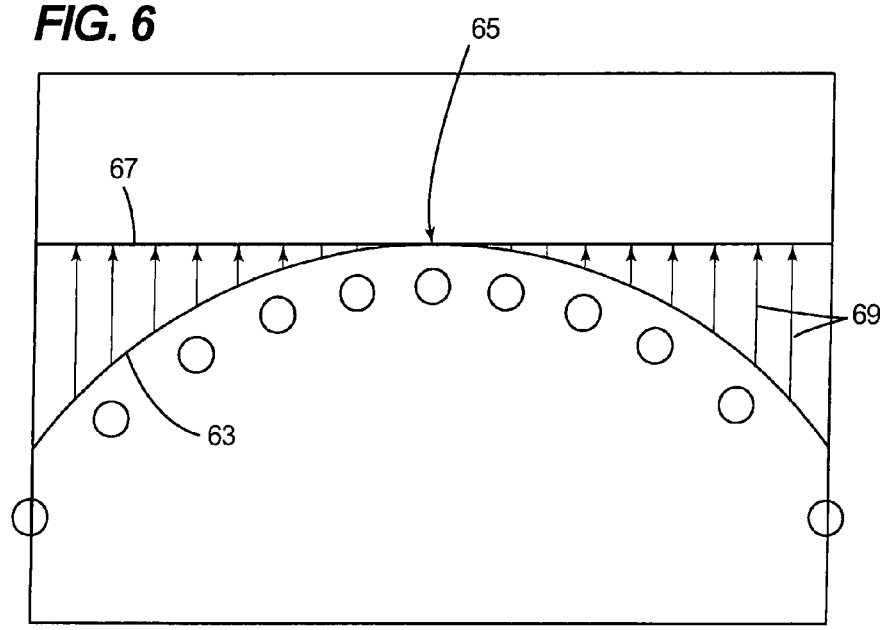
FIG. 6 is a schematic illustration of the unwrapping process illustrated in FIG. 4.

To start an inspection, the machine will transfer a container to the inspection station and following a time sufficient for the rotation of the container 10 to become stable, the Control 50 (FIGS. 4, 11 and 12) will begin the inspection. The Control will Rotate The Container About Axis Through Desired Angle 42 (FIG. 4). FIG. 5 illustrates the appearance of an anomaly 30 (a check or a blister) on the finish of the container, as it would appear if captured by the camera as the bottle rotated through θ (theta) degree increments. As illustrated, the container has an anomaly which is captured at ten of the eleven locations spaced θ (theta) degrees. Such could occur by operating the camera every time the bottle rotates θ (theta) degrees or could occur by holding the camera open for a prolonged period while strobing the light source each θ (theta) degrees. The anomalies are shown located within an angle of interest φ (phi) defining a partial elliptical path. The Control 50 proceeds to Capture A Selected Number Of Images At θ (theta) Degree Increments 44 and the Control will then Locate The Upper Edge Points Of Container 60. This edge 61 is shown in FIG. 5. The Control will then Fit Curve 62 to these edge points. This could be done using linear regression techniques. The fit curve 63 is shown in FIG. 6. The Control then proceeds to Determine Vertical Peak Of Fitted Curve 64. This peak 65 is also shown in FIG. 6. The Control than proceeds to Define Horizontal Line Through Peak 66 (line 67 in FIG. 6) and proceeds to Unwrap Image 68. This procedure is shown in FIG. 6 with vertical offsets 69 which are defined by the number of pixels required to shift the fitted curve 63, at each vertical row, vertically to the peak tangent line 67. The Control will then Define The Center Of An Anomaly In Each Captured Image 46.

Figure 7:
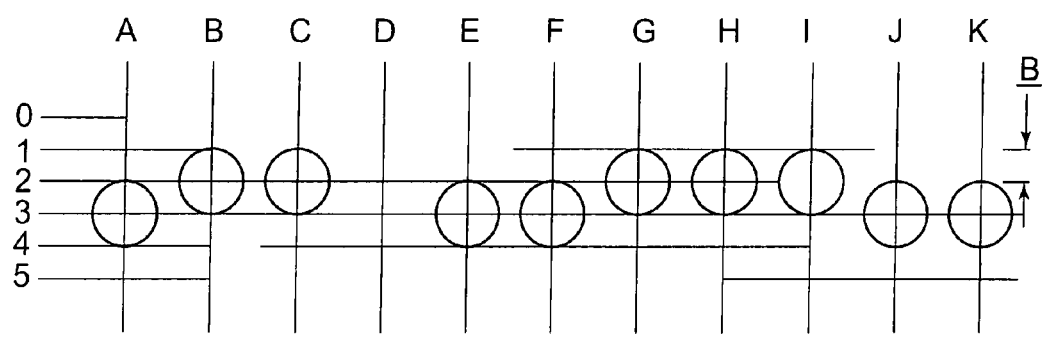
FIG. 7 is a presentation of 10 images of an object captured through 11 locations spaced θ (theta) degrees apart through an angle of φ (phi) degrees with the center of the object plotted.
Figure 8:
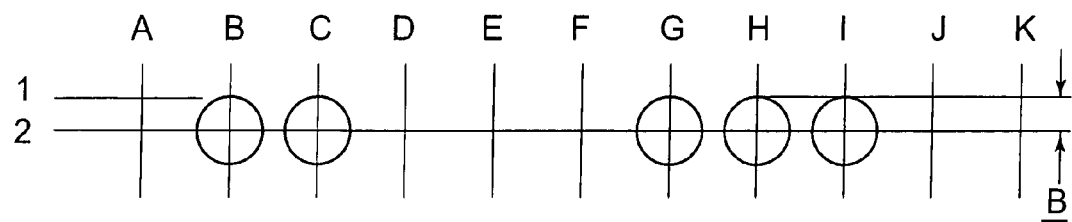
FIG. 8 is presentation similar to that of FIG. 7 showing only the objects in band 1-2.
Figure 9:
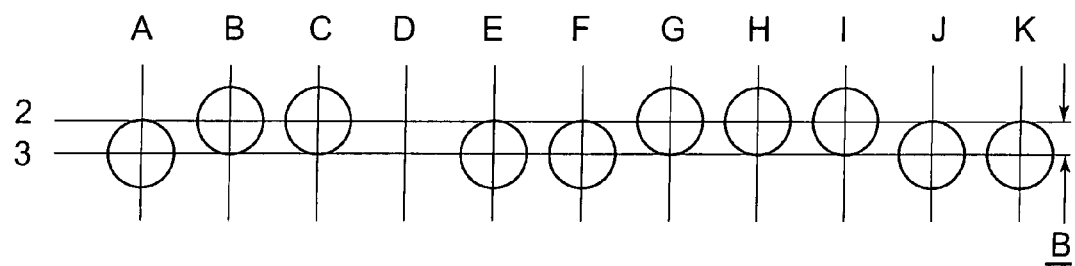
FIG. 9 is presentation similar to that of FIG. 7 showing only the objects in band 2-3.
Figure 10:
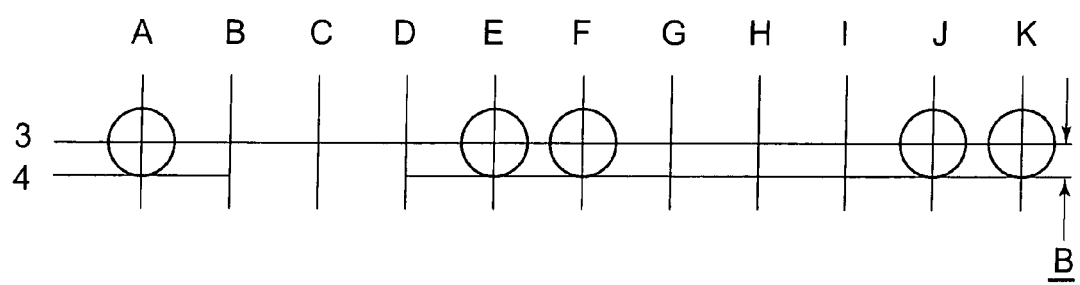
FIG. 10 is presentation similar to that of FIG. 7 showing only the objects in band 3-4.
Figure 11:
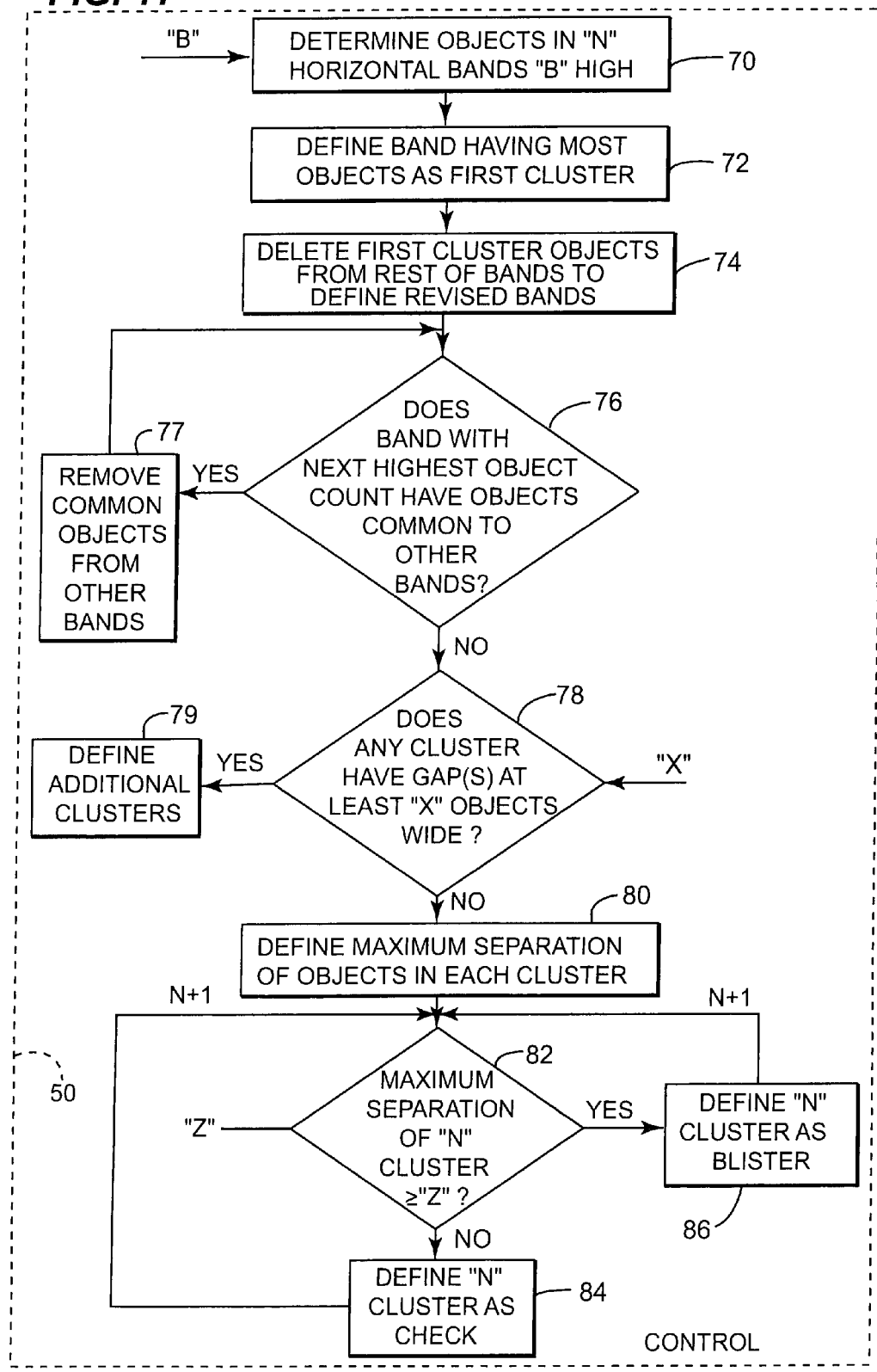
FIG. 11 is a control drawing showing the structure of the control for determining whether a captured object is a check or a blister.

FIG. 7 is a schematic presentation of the linear array of the ten images of an object captured through the 11 locations spaced θ (theta) degrees apart through the angle φ (phi) degrees with the center of the objects plotted showing their "Y" location as a function of three horizontal bands and with their "X" location corresponding to its angular increment. While the preferred embodiment unwraps the elliptical image to define horizontal bands, the bands could be elliptically matched to the pattern of the captured objects. FIGS. 8-10 are schematic presentations of the objects sorted into each of the bands (1-2, 2-3, and 3-4) presented in FIG. 7. Each band represents a horizontal scan line or lines (a band could, for example be five horizontal scan lines). The width of each band ("B") is shown as settable. Referring to FIG. 11, the Control 50 will Determine Objects In "N" Horizontal Bands "B" High 70. The objects within a band define a "cluster". The cluster objects identified in FIGS. 8 through 10 are:

Band 1 (1-2)—objects B, C, G, H, I;
Band 2 (2-3)—objects A, B, C, E, F, G, H, I, J, K;
Band 3 (3-4)—objects A, E, F, J, K;

The Control then proceeds to Define Band Having Most Objects As First Cluster 72. In the above illustration, Band 2 has the most objects (10). If two bands have an identical number, the Control could pick either one first. The Control then proceeds to Remove Common Objects From Other Bands 74. The bands thus become:

Band 2 (2-3)—objects A, B, C, E, F, G, H, I, J, K;

When the Control asks the query Does Band With Next Highest Count Of Objects Have Objects Common To Other Bands? 76, the answer will be in the negative—Band 2 has all the unique objects. No further revisions of the bands will take place. The objects in Band 2 will then be identified as a cluster.

Alternately, the bandwidth "B" could be set at 10 scan lines and all of the ten objects could be located within the single band and treated as a single cluster.

The Control next asks Does Any Cluster Have Gap(s) at least "X" Objects Wide (X is settable) 78. In the event the query is answered in the affirmative, the Control will Define Additional Clusters 79. If "X" was set at three, this query for Band 2, would be answered in the negative since there is a single gap one object wide. Had this gap been three objects wide (D, E, & F missing, for example) the Control would define the objects to the left of the gap (A, B, & C) as one cluster and the objects to the right of the gap (G-K) as a second cluster. It has been found that blisters generally have very small gaps and that a large gap indicates one or more checks. If the operator does not want to use this tool, "X" can be set at 12, for example.

The Control will then Define Maximum Separation Of Objects In Each Cluster 80. Cluster 1 has ten spacings separating A from K. The Control now determines whether the cluster is a check or a blister. This is done by answering the query "Max Separation of "N" Cluster≧(greater than or equal to) "Z"?" 82. Assuming Z is 8 (a settable input), when this inquiry is answered for Cluster 1 the answer will be yes and the Control will Define "N" Cluster As Blister 86. Had the separation been less than 8, the Control would Define "N" Cluster As Check 84. This procedure will be repeated for each cluster.

Figure 12:
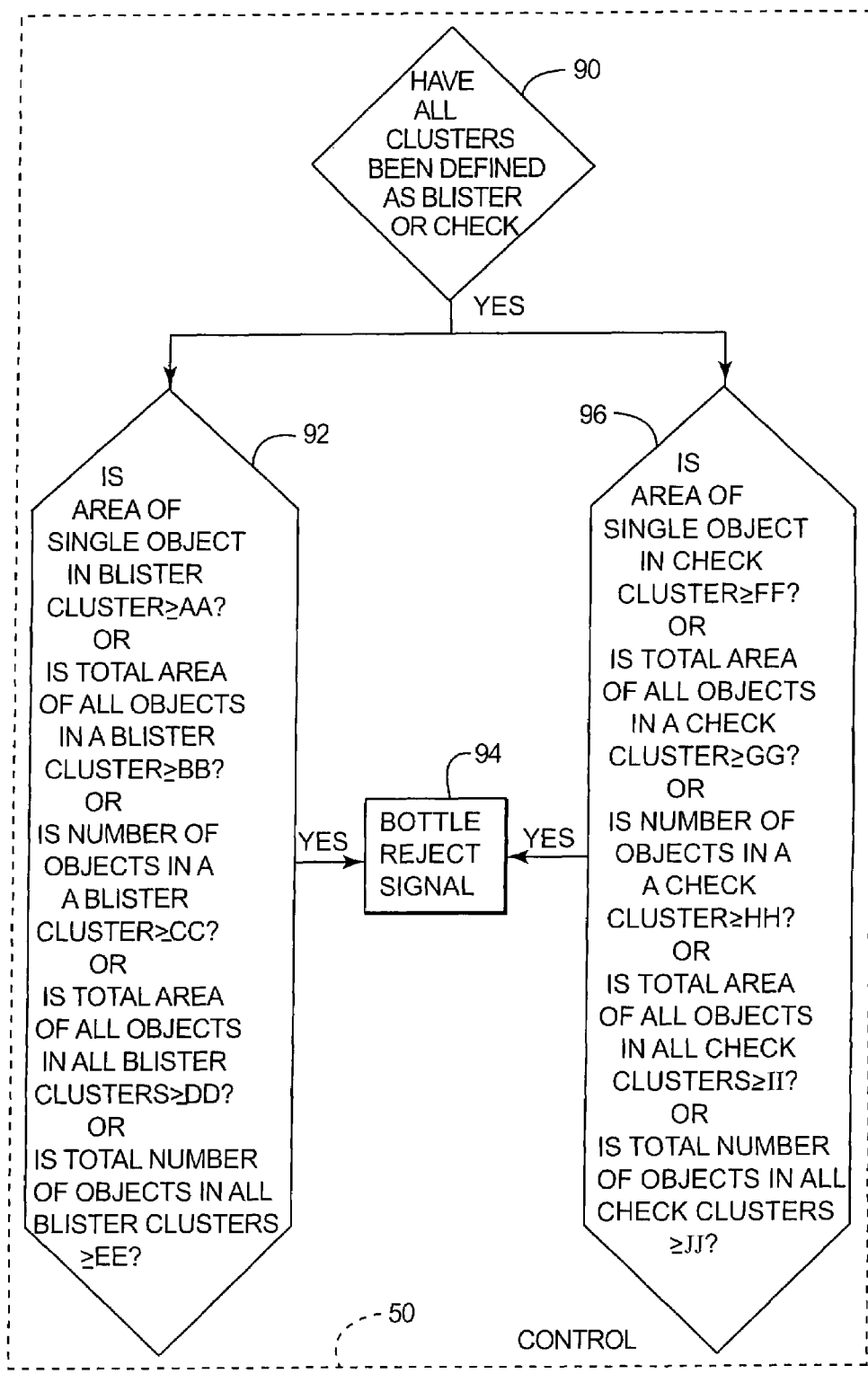
FIG. 12 is a control drawing illustrating the structure for identifying a bottle for rejection.

If desired, a decision could be made at this point to pass all blisters and reject all checks but additional choices are provided by the Control. FIG. 12 illustrates the structure of the Control 50 for discriminating between a Blister or Check that will not result in a bottle being rejected and one that will. The Control answers the query "Have All Clusters Been Defined As A Blister Or A Check? 90". If the answer is "yes", the Control answers the query "Is Area Of Single Object In A Blister Cluster≧(greater than or equal to) AA" Or Is Total Area Of All Objects In A Blister Cluster≧(greater than or equal to) BB? Or Is Number Of Objects In A Blister Cluster≧ (greater than or equal to) CC? or Is Total Area Of All Objects In All Blister Clusters≧(greater than or equal to) DD? Or Is Total Number Of Objects In All Blister Clusters≧(greater than or equal to) EE? 92. If this query is answered in the affirmative, the Control will issue a Bottle Reject Signal 94.

The Control will also answer the query "Is Area Of Single Object In Check Cluster≧(greater than or equal to) FF?" Or Is Total Area Of All Objects In A Check Cluster≧(greater than or equal to) GG? Or Is Number Of Objects In A Check Cluster≧(greater than or equal to) HH? or Is Total Area Of All Objects In All Check Clusters≧(greater than or equal to) II? Or Is Total Number Of Objects In All Check Clusters≧ (greater than or equal to) JJ? 96. If this query is answered in the affirmative, the Control will also issue a Bottle Reject Signal 94.

The invention claimed is:

1. A machine for inspecting the finish area of a glass container rotating at an inspection station and discriminating between blisters and checks comprising;
    a rotating device for rotating a bottle about its axis;
    a lighting device for illuminating the finish area of the rotating bottle;
    a camera for imaging the finish area of the rotating bottle; and
    a control configured to:
        define an array of objects captured by said camera at a predetermined number of angular increments of rotation;
        define a plurality of adjacent bands which include the captured objects; and
        analyze the adjacent bands to identify a check or a blister;
    wherein said control configured to analyze the adjacent bands to identify a check or a blister comprises means for defining clusters of captured objects including:
        means for determining the band having the most captured objects;
        means for deleting the objects in the band having the most objects from the rest of the bands which include objects; and
        means for repeatedly determining the band of the rest of the bands having the most objects and deleting the objects in the band of the rest of the bands having the most objects from the remainder of the bands until the objects in each band are unique, the unique objects in each band defining a cluster.

2. A machine for inspecting the finish area of a glass container rotating at an inspection station and discriminating between blisters and checks according to claim 1, wherein said bands are horizontal bands.

3. A machine for inspecting the finish area of a glass container rotating at an inspection station and discriminating between blisters and checks according to claim 1, wherein said control configured to analyze the adjacent bands to identify a check or a blister further comprises;
   means for determining whether there is at least one gap having a minimum size between objects in each cluster; and
   means for defining additional clusters as a function of the number of such gaps.

4. A machine for inspecting the finish area of a glass container rotating at an inspection station and discriminating between blisters and checks according to claim 1, wherein said control for analyzing the adjacent bands to identify a check or a blister further comprises;
   means for defining a selected separation of objects in a cluster;
   means for determining the separation of the farthest separated objects in a cluster; and
   means for defining the cluster as a check where separation of the farthest separated objects in the cluster is less than the selected separation.

5. A machine for inspecting the finish area of a glass container rotating at an inspection station and discriminating between blisters and checks according to claim 4, wherein a cluster is defined as a check, said control further comprises
   means for determining the area of the largest object in the cluster and
   means for generating a reject signal in the event the largest object area exceeds a predetermined area.

6. A machine for inspecting the finish area of a glass container rotating at an inspection station and discriminating between blisters and checks according to claim 4, wherein a cluster is defined as a check, said control further comprises
   means for determining the total area of all objects in the cluster and
   means for generating a reject signal in the event the total area exceeds a predetermined area.

7. A machine for inspecting the finish area of a glass container rotating at an inspection station and discriminating between blisters and checks according to claim 4, wherein a cluster is defined as a check, said control further comprises
   means for determining the number of objects in the cluster and
   means for generating a reject signal in the event that the number of objects in the cluster exceeds a predetermined number.

8. A machine for inspecting the finish area of a glass container rotating at an inspection station and discriminating between blisters and checks according to claim 4, wherein all check clusters have been defined, said control further comprises
   means for determining the total area of all objects in all of the clusters wherein the object has been defined as a check and
   means for generating a reject signal in the event the total area exceeds a predetermined area.

9. A machine for inspecting the finish area of a glass container rotating at an inspection station and discriminating between blisters and checks according to claim 4, wherein all of the check clusters have been identified, said control further comprises
   means for determining the total number of objects in all clusters defined as a check and
   means for generating a reject signal in the event that the total number of objects in all of the clusters defined as a check exceeds a predetermined number.

10. A machine for inspecting the finish area of a glass container rotating at an inspection station and discriminating between blisters and checks according to claim 4, wherein said control further comprises
    means for defining a cluster as a blister where the furthest separated objects in the cluster are separated by at least the selected separation.

11. A machine for inspecting the finish area of a glass container rotating at an inspection station and discriminating between blisters and checks according to claim 10, wherein a cluster is defined as a blister, said control further comprises
    means for determining the area of the largest object in the cluster and
    means for generating a reject signal in the event the largest object area exceeds a predetermined area.

12. A machine for inspecting the finish area of a glass container rotating at an inspection station and discriminating between blisters and checks according to claim 10, wherein a cluster is defined as a blister, said control further comprises
    means for determining the total area of all objects in the cluster and
    means for generating a reject signal in the event the total area exceeds a predetermined area.

13. A machine for inspecting the finish area of a glass container rotating at an inspection station and discriminating between blisters and checks according to claim 10, wherein a cluster is defined as a blister, said control further comprises;
    means for determining the number of objects in a cluster; and
    means for generating a reject signal in the event that the number of objects in the cluster exceeds a predetermined number.

14. A machine for inspecting the finish area of a glass container rotating at an inspection station and discriminating between blisters and checks according to claim 10, wherein all blister clusters have been identified, said control further comprises
    means for determining the total area of all objects in all of the clusters wherein the object has been defined as a blister and
    means for generating a reject signal in the event the total area exceeds a predetermined area.

15. A machine for inspecting the finish area of a glass container rotating at an inspection station and discriminating between blisters and checks according to claim 10, wherein all blister clusters have been identified, said control further comprises
    means for determining the total number of objects in all of the clusters identified as a blister and
    means for generating a reject signal in the event that the total number of objects in all of the clusters defined as a blister exceeds a predetermined number.

* * * * *